United States Patent [19]

Salerno

[11] Patent Number: 5,394,865
[45] Date of Patent: Mar. 7, 1995

[54] FIBER-VIEW LIGHTED STYLET

[76] Inventor: Albert Salerno, 10830 Carla Pl., Cerritos, Calif. 90701

[21] Appl. No.: 118,894

[22] Filed: Sep. 9, 1993

Related U.S. Application Data

[63] Continuation-in-part of Ser. No. 998,396, Dec. 28, 1992, Pat. No. 5,337,735.

[51] Int. Cl.$^6$ .................................................. A61B 1/06
[52] U.S. Cl. .......................................... 128/11; 128/6
[58] Field of Search ..................... 128/6, 7, 10, 11, 16, 128/22, 23; 385/115, 116, 117

[56] References Cited

U.S. PATENT DOCUMENTS

| | | |
|---|---|---|
| 297,363 | 8/1888 | Salerno et al. . |
| 543,616 | 7/1895 | Dow . |
| 2,289,226 | 7/1942 | Von Foregger . |
| 3,281,637 | 10/1966 | Hultquist . |
| 3,739,769 | 6/1973 | Kaye . |
| 3,941,121 | 3/1976 | Olinger et al. . |
| 3,986,854 | 10/1976 | Scrivo et al. . |
| 4,273,112 | 6/1981 | Heine et al. . |
| 4,320,745 | 3/1982 | Bhitiyakul et al. . |
| 4,406,280 | 9/1983 | Upsher . |
| 4,583,527 | 4/1986 | Musicant et al. . |
| 4,583,528 | 4/1986 | Bailman .............................. 128/11 |
| 4,924,855 | 5/1990 | Salerno et al. . |
| 5,183,031 | 2/1993 | Rossoff . |

Primary Examiner—Richard J. Apley
Assistant Examiner—Beverly A. Meindl
Attorney, Agent, or Firm—Trask, Britt & Rossa

[57] ABSTRACT

Disclosed is an autoclavable fiber-illuminated stylet and visual probe useful in assisting in the performance of intubations and other medical procedures. The stylet has a removably attached handle having a light source from which extends encased, malleable fiber-optic cables capable of transmitting light to the local area to be seen (e.g. in the vicinity of the epiglottis). The local are may be viewed through a removably attached scope via the second fiber optic cable.

20 Claims, 5 Drawing Sheets

FIBER-VIEW LIGHTED STYLET

CROSS-REFERENCE TO RELATED APPLICATION

This application is a continuation-in-part of U.S. Ser. No. 07/998,396, filed on Dec. 28, 1992, now U.S. Pat. No. 5,337,735.

TECHNICAL FIELD

The present invention relates to medical or dental instruments generally, and to an autoclavable, removably attached, illuminated stylet having an encased fiber-optic cable for viewing extending therefrom specifically.

BACKGROUND

During a medical intubation procedure, a tube is inserted into an orifice or hollow organ such as the larynx to allow for the administration of gases or to admit air. Unfortunately, the procedure sometimes goes amiss, and the tube is inserted into the wrong orifice (e.g., leading to the digestive rather than the respiratory tract).

Although illuminated laryngoscopes are available (see, e.g. U.S. Pat. No. 3,986,854 to Scrivo et al., U.S. Pat. No. 4,583,527 to Musicant et al., U.S. Des. Pat. No. 297,363 to Salerno et al., and U.S. Pat. No. 4,924,855 to Salerno et al.), the scope of illumination is somewhat inherently limited by the length of the laryngoscope blade. The prior art also discloses an fiberoptic intubating laryngoscope incorporating a "goose neck" stylet. (U.S. Pat. No. 5,183,031 to Rossoff).

It would be an improvement in the art if a device were available for safely illuminating and viewing an intubation procedure, especially in the lower part of the pharynx, and if the device could be easily sterilized by autoclaving. Additionally, it would be a further improvement if such a device had a means for attaching stylets of varying lengths, depending on the application requirements, to an easily grasped handle.

DISCLOSURE OF THE INVENTION

The invention includes an instrument for illuminating and viewing a local area. The instrument includes: a handle having two ends and a removably attached encased probe containing two flexible, fiber optic cables, the fiber optic cables associated at their first ends with one end of the handle and extending from the handle together to the local area. The first fiber optic cable extends from the distal end of the handle and conducts light from a light source to the local area. The second fiber optic cable extends from a detachable scope associated with the handle along with the first fiber Optic cable to the local area, thus enabling a user to simultaneously illuminate and view the local area with the probe. At least one fiber optic cable is encased within a malleable casing.

The instrument may have, enclosed within the handle, an energy source, a light source, or both. Alternatively, both or either of these may be external to the device. The instrument may also have a switch for controlling illumination and extinguishment of the light source.

The instrument is ideally suited to illuminate an intubation or similar procedure. The instrument has a malleable stylet (or probe) and utilizes the advantages of fiber optics which include keeping the light source external to the patient and securely attached to the handle. The local area illuminated by the light source and associated fiber optic cable can also be viewed by the user through the scope via the second fiber optic cable.

Once the probe has been shaped into the desired conformation, the probe portion has the characteristic of maintaining the selected formation until later manipulation.

BRIEF DESCRIPTION OF THE FIGURES

In the drawings, Which depict presently preferred embodiments of the invention and in which like reference numerals refer to like parts in different views.

BEST MODE OF THE INVENTION

Figure 1:
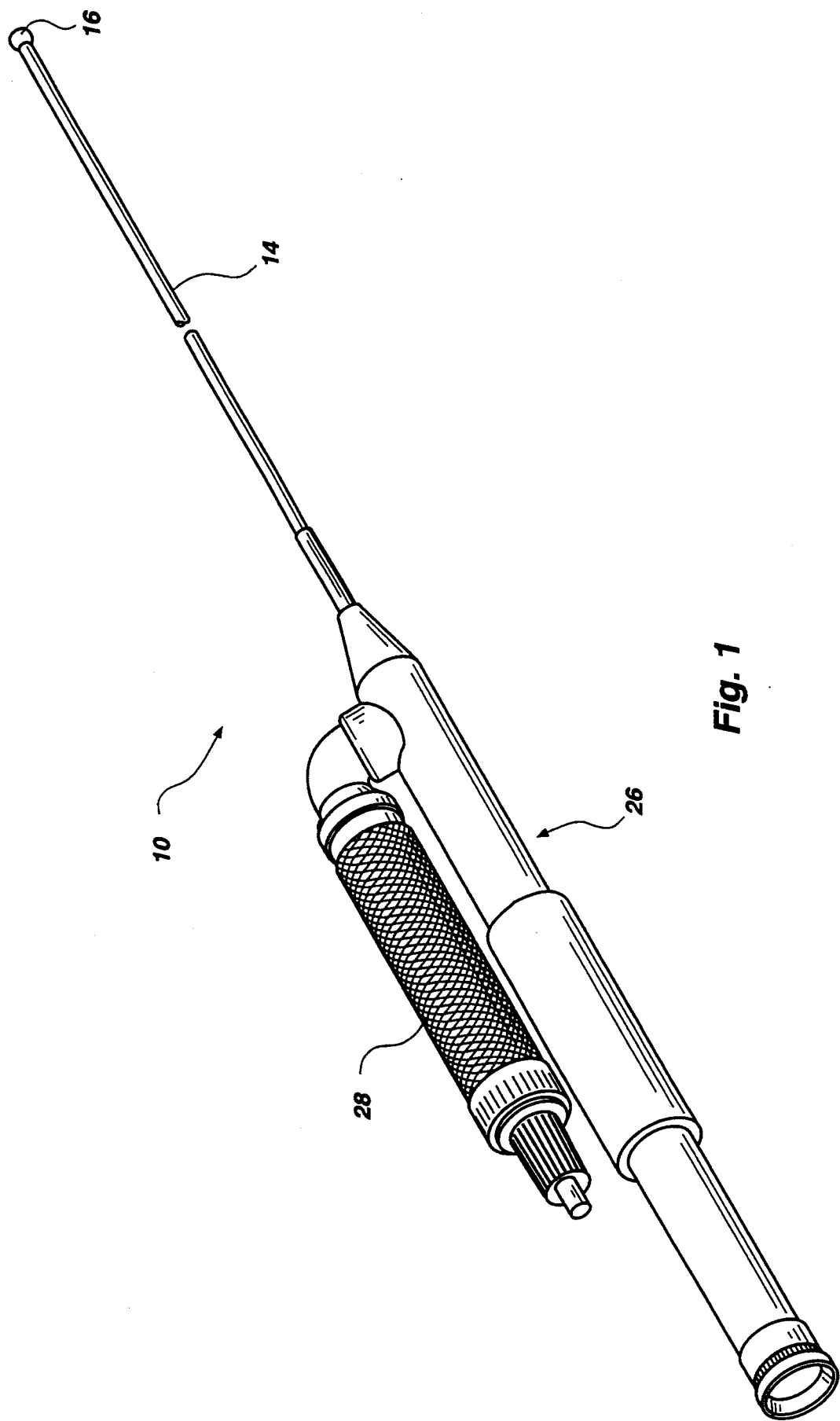
FIG. 1 is a side view of a preferred instrument in accordance with the invention.

As shown in FIG. 1, a preferred device according to the invention, generally 10, has a handle, generally 12. The handle 12 is detachably associated with a probe 14 extending from the handle 12 terminating at an end point 16.

Figure 5:
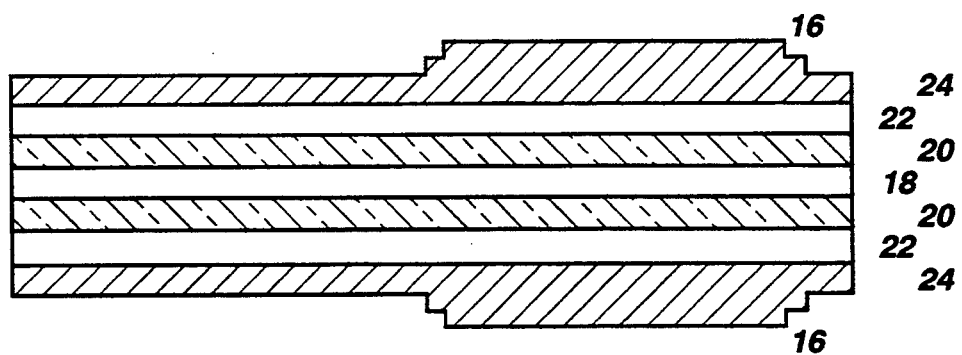
FIG. 5 is a magnified longitudinal cross-sectional view of a probe according to the invention, taken along Section-line 5—5 of FIG. 3.

The probe 14 includes a first fiber optic cable 18 encased within a flexible of malleable, preferably opaque, material 20 (FIG. 5). Surrounding the encased first fiber cable 18 is a second fiber optic cable or cables 22. As can be seen, this second fiber optic cable is preferably annular in cross-section, and is further preferably concentric with the first fiber optic cable in a coaxial arrangement. This second fiber optic cable 22 is also enclosed within a malleable or flexible, preferably opaque, material 24. The materials which encase the fibers can be the same or different. A coaxial arrangement of the two fiber optic cables allows a smaller total probe diameter, enabling easier access through narrow cavities; the coaxial configuration also provides a more uniform illumination of the local area.

Figure 2:
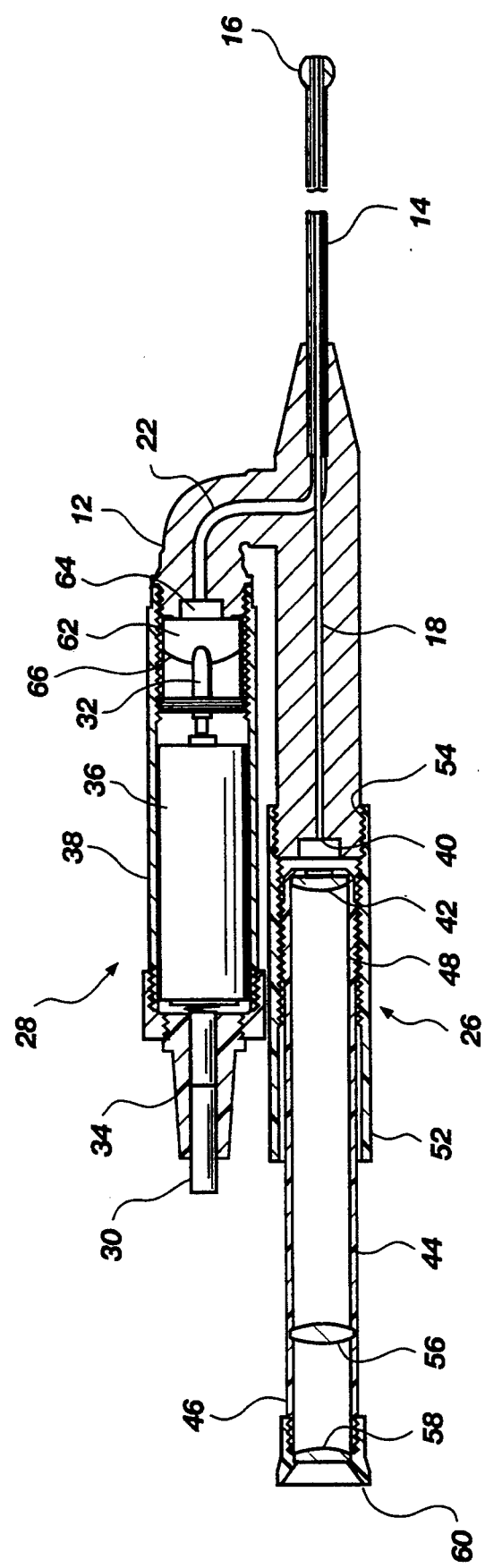
FIG. 2 is a cut-away view of a preferred instrument according to the invention.

As can best be seen in FIG. 2, the handle can be considered as including a detachable viewing portion 26 and a detachable illuminating portion 28. The entire handle is preferably sized to fit comfortably within the user's hand. The handle employs a cylindrical design which allows the user to have greater control in directing the stylet; the handle may be grasped like a pen, thereby allowing the user to exercise delicate control in positioning of the probe.

In one preferred embodiment, the handle is made of stainless steel, although other materials, especially those capable of conducting a current, may be used. Materials useful for making the handle include: brass, aluminum, plastic, and stainless steel. The exterior surface of a portion of the handle may be gnarled or rough (e.g. FIG. 3) in order to provide a more secure grip for a user.

To the viewing portion or scope may be associated a camera, video camera or other similar device for both allowing more than one person to view the procedure and to allow whatever procedure is being performed with the device to be recorded.

The illuminating portion of the handle, generally 28, preferably is associated with a switch 30. This switch 30 controls the illumination of a light source 32 preferably mounted in or on the illuminating portion of the handle. In the depicted embodiment, the switch 30 has a base portion 32 made of an insulating material (e.g. plastic), and, similar to a flashlight, when the button 30 is pressed, a circuit is completed between a power source (e.g. battery 36 or a power source external to the device) and the light source 32, using a electrically conducting handle 38 to complete the circuit. An ideal switch for use with the depicted device is one which turns on and off or one which pushes on and pulls off. Commercially available switches may be used or readily adapted for use. The positioning of the switch at the proximal end of the handle permits the user to operate the switch using his or her thumb with a minimum of hand movement and accompanying loss of control of the instrument.

In the depicted embodiment, a fiber optic cable 22 extends from the light source 32 through a portion of the handle to form part of the probe 14 (FIG. 2). This fiber optic cable 22 transmits light from the light source to the local area to be illuminated proximate the probe's bulbous end 16.

The illuminating fiber optic cable 22 forms part of the probe along with the other fiber optic cable 18. This other fiber optic cable 18 is used to view the local area to be illuminated. It runs from the probe's bulbous end 16, down the center of the probe to form an optical face 40 positioned within the handle's viewing portion 26. The optical face 40 abuts a lens 42. The lens 42 has a convex portion, and is fixed within a scope 44.

The scope 44 includes a proximal end 46 and a distal end 48 which contains the lens 42. The distal end 48 of the scope has outer threads 50 which coact with a tube 52 having inner threads 54. The threads 50, 54 allow a user of the device to focus the scope 44 finely in order to view the area as clearly as possible. The scope 44 may also include a second lens 56, and a third lens 58 contained within an eye piece 60 placed at the proximal end of the scope 46. The scope 44 is removably attached to the handle of the fiberoptic probe by the inner threads 54.

The fiber optic cables 18, 22 are flexible at room temperature and each can be a single cable, or may consist of a bundle of smaller cables. The cables are of a sufficient diameter and quality to transmit light for illuminating and viewing the desired local area. A typical cable has a diameter of from one to four millimeters, preferably 3.0 to 3.1 mm, or may be a bundle of smaller cables having a similar diameter. Fiber optic cables suitable for use with the invention can be purchased from Amtec Medical Products.

The material encasing the cables is a material, malleable at room temperature at the thickness chosen, such as stainless steel, brass or malleable iron. The thickness of the casings themselves will typically vary from 0.45 to 0.9 mm, and will be sufficiently thick to be malleable, but somewhat rigid. Once bent into its desired conformation, the probe 14 will generally remain in that position until it is again manipulated by the user to a different position. The casing 20, 24 coats or encases the fiber optic cables along their longitudinal portion like a pipe, and have two open ends to permit the passage of light from the light source 32 through the probe to the end point 16. Such an arrangement allows the instrument to project light out into or onto a local area adjacent (within, for example, at least 0.5 cm directly in front of) the end point 16. The fiber-optic cables can be slipped into, or otherwise encased within, the tubular encasing material. The encased cables will typically have a length ranging from twenty to forty-five centimeters, preferably twenty-five to thirty-three centimeters, although practically any chosen length can be used, and various lengths may be attached to the handle as particular applications dictate.

The light source can be a lamp, bulb, or similar device. In the depicted device (FIG. 2), the bulb (e.g. a 2.7 volt bulb from Amtec Medical Products) is powered by a battery 36 (Duracell 4.05 volt Mercury Battery). The light from the light source projects up a small cylinder 62 to the optical face 64 of cable 22. The light source may be centered within a parabolic reflector 66 which directs the light towards the bottom (optical face) 64 of cable 22.

In another embodiment (not depicted) the light source is light transmitted (e.g. by a fiber-optic cable) from a source distinct from the handle to the bottom (optical face) 64 of the cable 22.

Whatever the light source, the bottom 64 of the encased cable constitutes an optical face. Accordingly, the light source is chosen to be of a sufficient power to transmit light through the optical face and cable 22 and adequately illuminate the local area. The strength of the light source required will thus depend somewhat on the transmission capability of the fiber 22, the area to be illuminated, and the strength of the power source.

Figure 3:
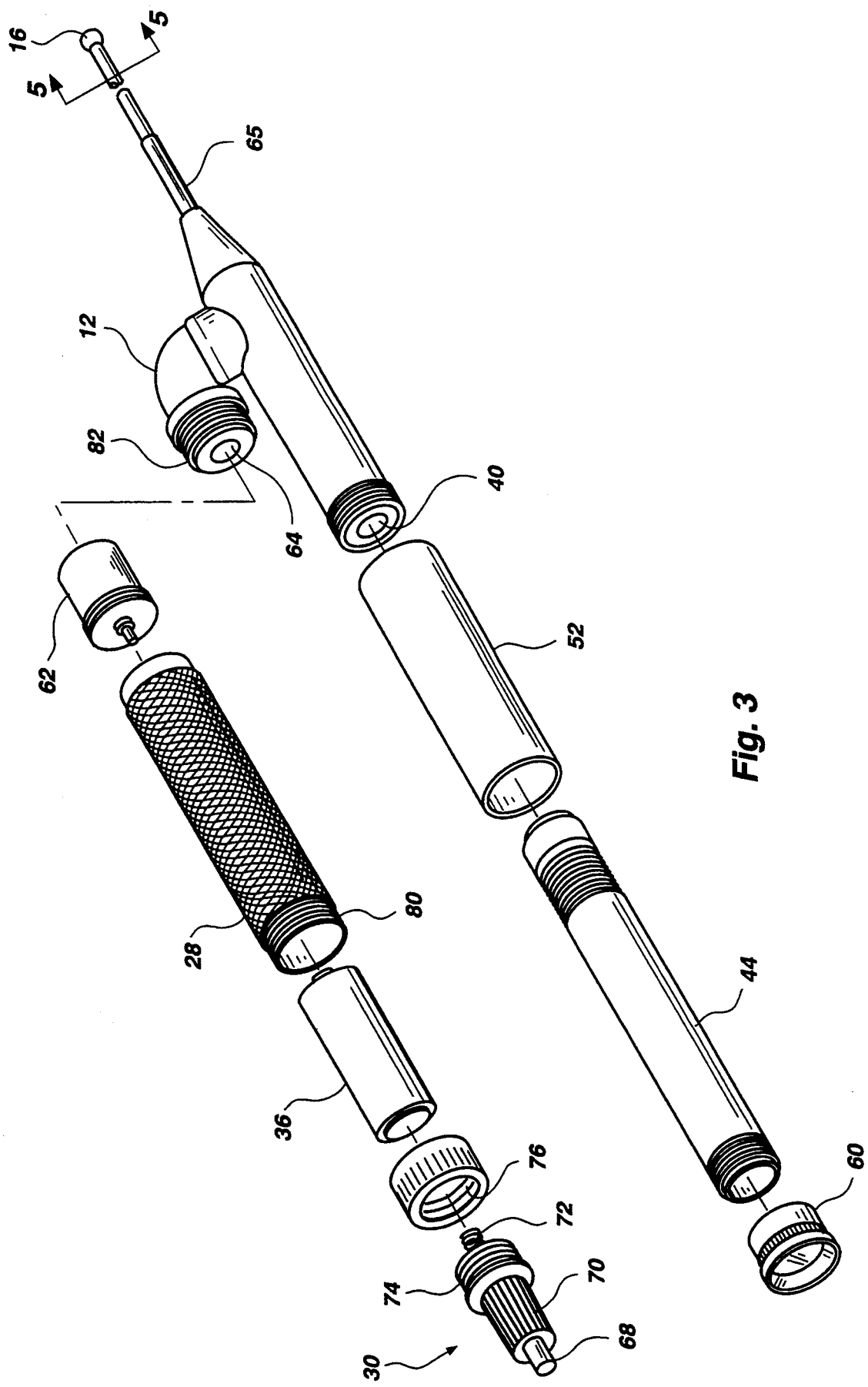
FIG. 3 is a side-view of a disassembled preferred instrument according to the invention.

FIG. 3 depicts a preferred embodiment of the device in a disassembled state, as it might be for sterilization. Starting from the proximal end of the device 10, a switch 30 is seen having a button 68, a plastic base 70 and a spring 72. The base 70 has threads 74 which interact with threads 76 inside cap 78. The cap 78 interacts with threads 80 of the handle's illuminating portion 28 to contain a battery 36 for powering the light source contained within cylinder 62. The cylinder 62 has inner threads (not shown) which interact with outer threads 82 on the removably attached base portion of the handle 12.

Starting at the optical face 64 found at the proximal end of the illuminating fiber 22, the illuminating fiber travels through the base of the handle 12 into the encased probe 14 (FIG. 2). In the embodiment depicted in FIG. 3, a portion of the probe is covered by a rubber-like sleeve 65. The probe 14 contains the encased cables 18, 22 and extends from the handle 12 for as long as desired, and preferably ends with a dull bulbous end 16. The dull bulbous end 16 is preferably made with a thickening of the casing material, although it need not be, and acts to help prevent injuries to the subject undergoing an intubation procedure with the probe.

Also travelling through the base of the handle 12 is the viewing fiber 18. This fiber 18 too ends at the bulbous end 16 of the probe, but begins at optical face 40 (FIGS. 2 and 3). As previously described, the scope which includes the eye piece 60, Scope body 44, tube 52, and associated lenses (not shown in FIG. 3) removably connects to the base portion of the handle 12 to allow a viewer peering through the eye piece 60 to see through the lenses 42, 56, 58 and the viewing fiber 18 to see the local area proximate the end of the probe 16.

FIG. 5 depicts a longitudinal, cross-sectional view of the probe 14 with its various components taken along section-line 5—5 of FIG. 3. In the center is the first fiber optic cable 18 for viewing. This cable 18 is encased within a flexible or malleable material 20 which is preferably opaque. The second fiber optic cable 22 for transmitting light from the light source to the local area coaxially surrounds the casing material 20. This illuminating fiber optic cable 22 is surrounded by a flexible or malleable, preferably opaque, material 24, which may be of the same or of a different composition as that of the material 20 encasing the first fiber optic cable 18. Either the material 20 encasing the first cable 18 or the material 24 encasing the illuminating fiber optic cable 22, or both, should be sufficiently malleable to retain the probe in a conformation once placed there by a user.

Figure 6:
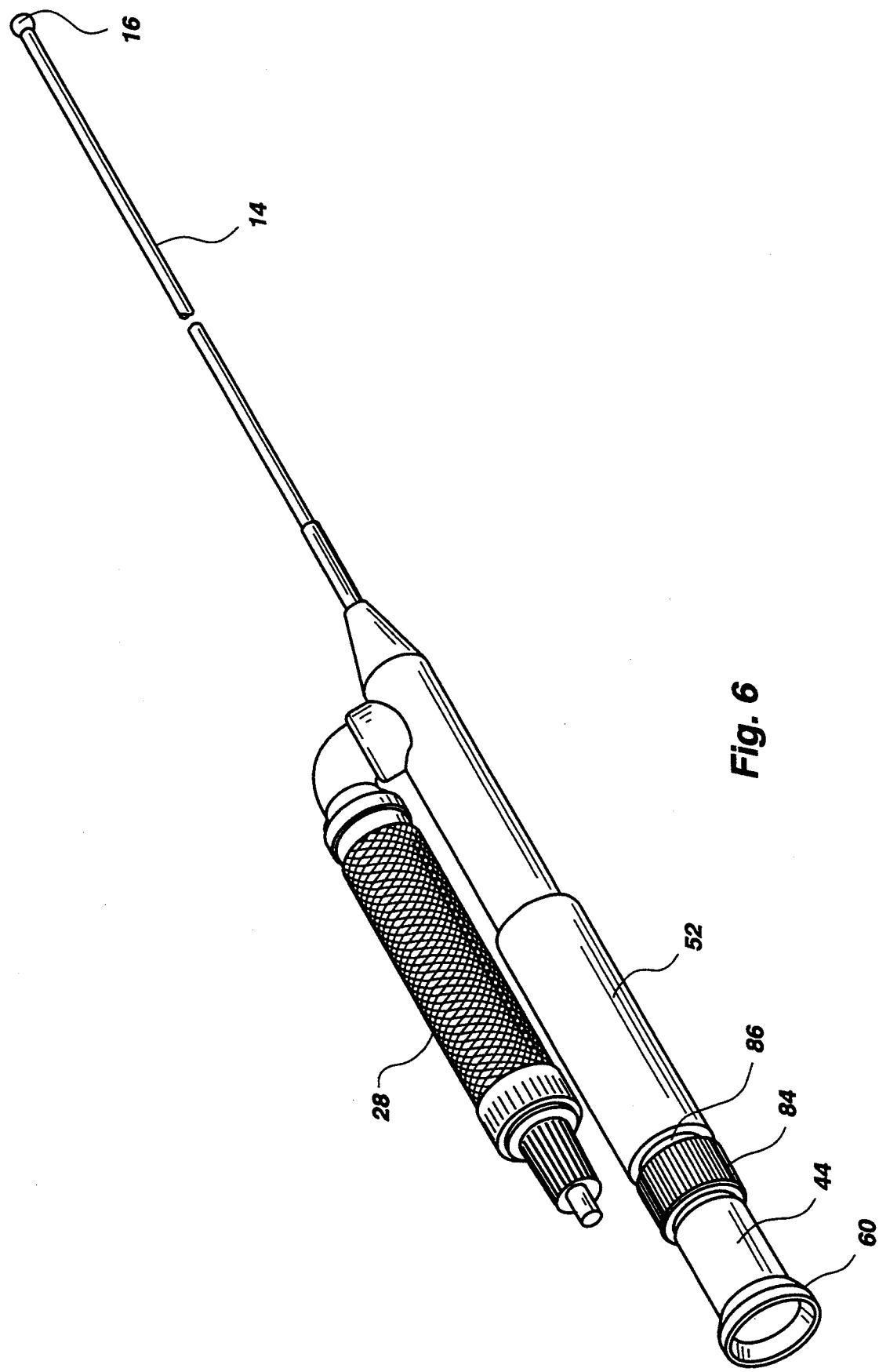
FIG. 6 is a side View of a preferred instrument according to the invention.

FIG. 6 depicts a presently preferred embodiment of the invention. This particular embodiment includes an internally threaded focusing tube 84, the inner threads of which interact with outer threads on the end of scope 44, and threads placed on second tube 86 which interact with inner threads contained within tube 52. Such an arrangement allows the device to be easily fine focused.

Figure 4:
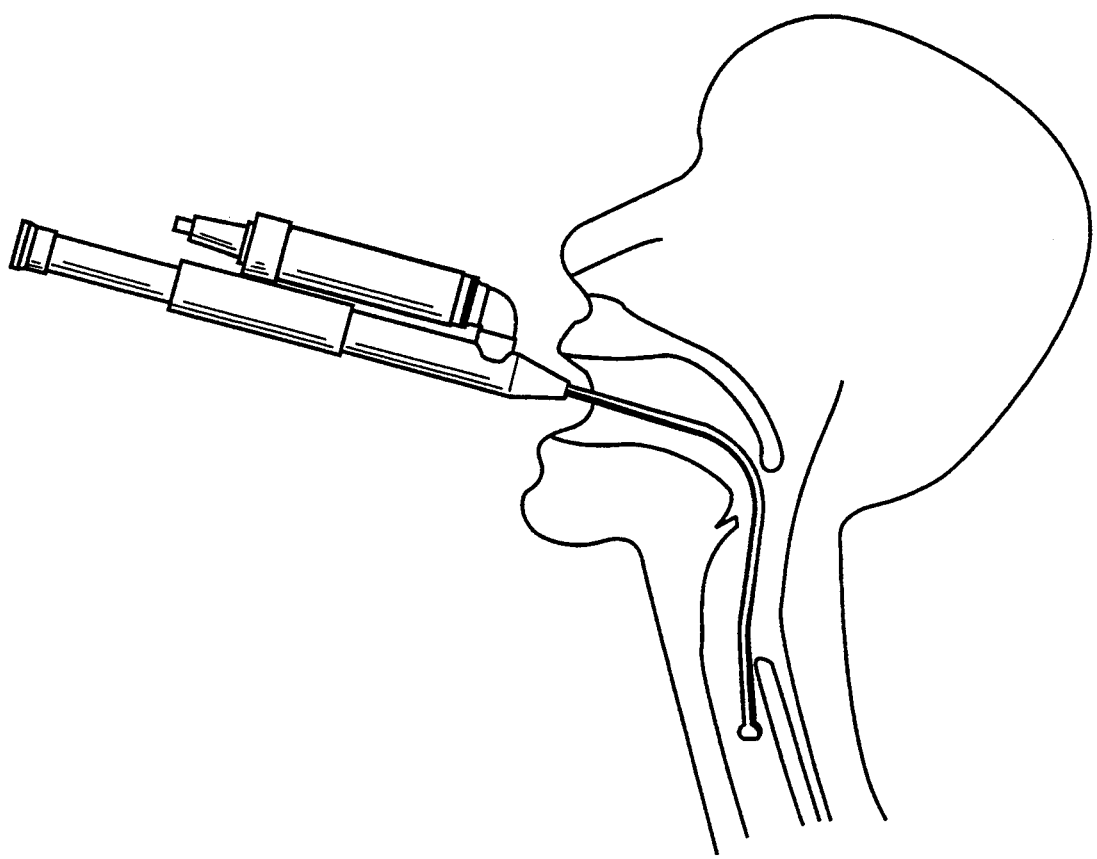
FIG. 4 is a view Of an instrument according to the invention in use.

For use in an intubation procedure, the instrument—or at least the probe—is, or already has been, preferably first sterilized, e.g. by autoclaving. The light source is then illuminated. The probe containing the fiber optic cables is bent to the desired conformation. It is then placed into the mouth of the subject and directed down the throat to the lower pharynx to illuminate the local area around the epiglottal area properly (FIG. 4). The physician performing the procedure may then peer through the eye piece of the scope to view the local area. The intubation device may then be directed down the subject's pharynx for proper placement while the physician observes the procedure. The device may also be used diagnostically to view the local area for the presence of, e.g. irritation or the formation of tumors.

Once the device according to the invention has been seen by one of skill in the art, methods and materials for making it will become readily apparent. For instance, the handle and cowl may be machined from commonly available metals or other materials. Batteries, fiber-optic cable, spring, light bulb, and switch may be purchased. The bulbous end portion of the casing may be welded. The ends of the fiber optic cables are preferably polished to form a better optical face.

Although the invention has been described with regard to certain preferred embodiments, the scope of the invention is to be defined by the appended claims.

What is claimed is:

1. An instrument for illuminating and viewing a local area comprising:
    a handle having first and second ends;
    first and second fiber optic cables, both of said fiber optic cables being flexible, and each having first and second ends, said fiber optic cables detachably associated at their first ends with the handle's second end and extending from the handle's second end to the local area;
    said first fiber optic cable extending from a light source through said handle to the local area and said second fiber optics cable extending from a removably attached scope associated with the handle through the handle to the local area; and
    means for encasing a portion of at least one of said fiber optic cables and for making said encased fiber optic cables malleable.

2. The instrument of claim 1 wherein the light source is enclosed within the handle.

3. The instrument of claim 2 further comprising a switch for controlling illumination and extinguishment of the light source placed at the first end of the handle.

4. The instrument of claim 3 wherein a portion of the handle is metallic, and said metallic handle portion completes a circuit between a battery, the switch, and the light source.

5. The instrument of claim 4 wherein the removably attached handle is cylindrically shaped.

6. The instrument of claim 2 wherein an energy source for said light source is enclosed within the handle.

7. The instrument of claim 2 wherein said light source is positioned within a cylindrical member.

8. The instrument of claim 7 wherein the light source is placed at the center of a parabolic reflector positioned within the cylindrical member said parabolic deflector directed towards said first send of said first fiber optic cable.

9. The instrument of claim 1 wherein the means for encasing the fiber optic cables is a malleable metal encasing one of the fiber optic cables.

10. The instrument of claim 1 further comprising means for focusing the scope.

11. The instrument of claim 1 wherein the means for encasing a portion of the fiber optic cable or cables encases both cables and is a malleable metallic material.

12. The instrument of claim 11 wherein the encased fiber optic cables terminate in a dull bulbous end.

13. The instrument of claim 1 wherein the second fiber optic cable is encased within an opaque flexible material, a concentric annular in cross-section first fiber optic cable, and a malleable, metallic material encasing a portion of said annular first fiber optic cable.

14. The instrument of claim 1 wherein said fiber optic cables are coaxially arranged, the first fiber optic cable surrounding the second fiber optic cable.

15. The instrument of claim 14 wherein a malleable material is positioned between said first fiber optic cable and said second fiber optic cable.

16. A method of illuminating a subject's larynx comprising using the instrument of claim 1.

17. An improvement in performing an intubation procedure being performed in a subject, the improvement comprising using the instrument of claim 1 to illuminate the subject's larynx.

18. An instrument for illuminating and viewing a local area comprising:
    a handle having first and second ends; and
    first and second fiber optic cables, both of said fiber optic cables being flexible, and each having first and second ends, said fiber optic cables detachably associated at their first ends with the handle's second end and extending from the handle's second end to the local area,
    said first fiber optic cable extending from a light source through said handle to the local area, said first fiber optic cable being concentricly annular in cross-section, and a portion of said first fiber optic cable being encased within a malleable, metallic material,
    said second fiber optic cable extending from a scope associated with the handle through the handle to the local area and said second fiber optic cable being encased within an opaque flexible material.

19. The instrument of claim 18 wherein a portion of the handle is metallic, and said metallic handle portion completes a circuit between a battery, the switch, and the light source.

20. The instrument of claim 18 further comprising means for focusing the scope.

* * * * *

UNITED STATES PATENT AND TRADEMARK OFFICE
CERTIFICATE OF CORRECTION

PATENT NO. : 5,394,865
DATED : March 7, 1995
INVENTOR(S) : Albert Salerno

It is certified that error appears in the above-indentified patent and that said Letters Patent is hereby corrected as shown below:

In the Abstract, line 7, change "are" to --area--;

In Column 5, line 64, after "a" insert --removably attached--;

In Column 5, line 66, change "optics" to --optic--

In Column 5, line 67, delete "removably attached";

In Column 6, lines 13-14, delete "removably attached";

In Column 6, line 22, change "deflector" to --reflector--; and

In Column 6, line 23, change "send" to --end--.

Signed and Sealed this

Seventh Day of November, 1995

Attest:

BRUCE LEHMAN

*Attesting Officer*     *Commissioner of Patents and Trademarks*